(12) United States Patent
Benquet et al.

(10) Patent No.: US 11,331,494 B2
(45) Date of Patent: May 17, 2022

(54) BRAIN TISSUE STIMULATION METHOD, APPARATUS AND COMPUTER PROGRAM

(71) Applicants: UNIVERSITE DE RENNES 1, Rennes (FR); INSTITUT NATIONAL DE LA SANTE ET DE LA RECHERCHE MEDICALE, Paris (FR)

(72) Inventors: Pascal Benquet, Montfort sur Meu (FR); Fabrice Wendling, Thorigne-Fouillard (FR); Julien Modolo, Dourdain (FR)

(73) Assignees: UNIVERSITE DE RENNES 1, Rennes (FR); INSTITUT NATIONAL DE LA SANTE ET DE LA RECHERCHE MEDICALE, Paris (FR)

( * ) Notice: Subject to any disclaimer, the term of this patent is extended or adjusted under 35 U.S.C. 154(b) by 94 days.

(21) Appl. No.: 16/090,443

(22) PCT Filed: Mar. 31, 2017

(86) PCT No.: PCT/EP2017/056920
§ 371 (c)(1),
(2) Date: Oct. 1, 2018

(87) PCT Pub. No.: WO2017/167636
PCT Pub. Date: Oct. 5, 2017

(65) Prior Publication Data
US 2019/0117980 A1 Apr. 25, 2019

(30) Foreign Application Priority Data
Mar. 31, 2016 (EP) .................................... 16000751

(51) Int. Cl.
*A61N 1/36* (2006.01)
*A61B 5/24* (2021.01)

(52) U.S. Cl.
CPC ............ *A61N 1/36171* (2013.01); *A61B 5/24* (2021.01); *A61N 1/36175* (2013.01); *A61N 1/36025* (2013.01)

(58) Field of Classification Search
CPC ............ A61N 1/36171; A61N 1/36025; A61N 1/3615; A61B 5/04001; A61B 5/24
See application file for complete search history.

(56) References Cited

U.S. PATENT DOCUMENTS 9,597,007 B2 * 3/2017 DeSalles .............. A61B 5/4047
2006/0217782 A1 9/2006 Boveja et al.
(Continued)

FOREIGN PATENT DOCUMENTS

EP 2331192 A1 6/2011
JP 2011-205576 A 1/2011
(Continued)

OTHER PUBLICATIONS

International Search Report dated Sep. 11, 2017 for corresponding International Application No. PCT/EP2017/056920, filed Sep. 11, 2017.
(Continued)

*Primary Examiner* — Unsu Jung
*Assistant Examiner* — Adreanne A. Arnold
(74) *Attorney, Agent, or Firm* — David D. Brush; Westman, Champlin & Koehler, P.A.

(57) ABSTRACT

A local stimulation method of a predetermined region of brain tissue, the brain tissue including at least GABAergic neuron type. The method includes at least one activation step of a set of bipolar electrodes, according to a predetermined electric intensity and a predetermined biphasic pulse fre-
(Continued)

quency, delivering a predetermined electric field. The predetermined electric field induces an activation of the GABAergic type neurons and a virtual absence of activation of other types of neurons.

11 Claims, 2 Drawing Sheets

(56) References Cited

U.S. PATENT DOCUMENTS

| | | | |
|---|---|---|---|
| 2007/0100378 A1* | 5/2007 | Maschino | A61N 1/36135 607/2 |
| 2010/0106207 A1* | 4/2010 | Dobak, III | A61K 38/2264 607/3 |
| 2011/0224752 A1* | 9/2011 | Rolston | A61N 1/0529 607/45 |
| 2012/0271189 A1 | 10/2012 | Nelson et al. | |
| 2017/0043166 A1* | 2/2017 | Choi | A61N 1/0534 |
| 2017/0113048 A1* | 4/2017 | Giftakis | A61N 1/36082 |

FOREIGN PATENT DOCUMENTS

| | | |
|---|---|---|
| WO | 2009059041 A1 | 5/2009 |
| WO | 2010025226 A1 | 3/2010 |
| WO | 2015048524 A1 | 4/2015 |

OTHER PUBLICATIONS

English translation of the Written Opinion dated Sep. 11, 2017 for corresponding International Application No. PCT/EP2017/056920, filed Sep. 11, 2017.
Decision of Rejection from corresponding Japanese Patent Application No. 2018-551866 dated Jul. 9, 2021.

* cited by examiner

BRAIN TISSUE STIMULATION METHOD, APPARATUS AND COMPUTER PROGRAM

CROSS-REFERENCE TO RELATED APPLICATIONS

This Application is a Section 371 National Stage Application of International Application No. PCT/EP2017/056920, filed Mar. 31, 2017, which is incorporated by reference in its entirety and published as WO 2017/167636 A2 on Oct. 5, 2017, in English.

1. FIELD

The technique pertains to the field of brain tissue stimulation. More specifically, the technique pertains to the field of stimulation of specific types of neurons in brain tissue.

2. PRIOR ART

A full understanding of the human brain is one of the greatest challenges in science. Such success would lead to major improvements in everyday life, among which new treatments for brain disease along with new computing technologies. The brain is able to receive, process, store and retrieve information; which is performed to a large extend by networks of neurons, communicating with each other through interfaces called synapses. Different neurotransmitters underlie the transmission of electrical impulsions at the level of synapses, and can be excitatory (favor neuronal activity) or inhibitory (decrease neuronal activity).

In the mammalian brain, every neuronal network features interconnected excitatory (using glutamate as their neurotransmitter) and inhibitory (using GABA, gamma-aminobutyric acid as their neurotransmitter) neurons. A dynamical balance between excitation and inhibition is required for the physiological functioning of networks. A transient hyperexcitability (i.e., positive excitation to inhibition ratio) can be physiological (learning, perception, memory . . . ); however, excessive and prolonged excitability due to synaptic inhibition failure is responsible for several neurological diseases. Therefore, evaluating the physiological response of GABAergic neurons is a way to quantify the level of network excitability, and determining if the tissue is healthy or hypexcitable (impaired GABAergic response). It is thus desirable to provide a solution which would enable recording the evoked response of GABAergic neurons.

It has to be noted that prior art solutions have already been proposed to evaluate the level of brain tissue excitability. However, these solutions do not enable stimulating only GABAergic neurons. This is for example the case of the method and device proposed in patent application EP 2331192 A1. Among the fact that the method proposed in this application is directed to treat epilepsy, this method fails in recording activity of GABAergic neuron only. Indeed, the proposed method (and electrodes) stimulates every cell in a given area, which is not desirable when trying to observe and record the functioning of these GABAergic neurons.

SUMMARY

The proposed technique does not have these drawbacks of prior art stimulation solutions. The proposed techniques enable the selective recording of GABAergic neurons activity. The proposed techniques may be employed for understanding the functioning of GABAergic neurons by avoiding a response from pyramidal neurons.

More specifically, a method and a device for stimulating GABAergic neurons are proposed. According to the present technique, the method comprises a plurality of steps of activation of a set of bipolar electrodes, at predetermined intensity, frequency and pulse length, delivering a predetermined electric field, said predetermined electric field inducing an activation of said GABAergic neurons and minimal activation of other type of neurons of said neural tissue.

The invention relates more specifically to a Local stimulation method of a predetermined region of brain tissue, said brain tissue comprising at least GABAergic neuron type. According to the invention said method comprises at least one activation step of a set of bipolar electrodes, according to a predetermined electric intensity and a predetermined biphasic pulse frequency, delivering a predetermined electric field, said predetermined electric field inducing an activation of said GABAergic type neurons and a virtual absence of activation of other types of neurons.

Thus, while delivering a predetermined electric field (being the spatial gradient of the electrical potential) between the anode and the cathode of the bipolar electrode, the proposed method allows stimulating specifically a type of neurons: GABAergic neurons.

According to a specific feature, the activation of said set of bipolar electrodes comprises delivering, to said bipolar electrodes, biphasic pulses, each biphasic pulse lasting about 200 microseconds.

According to a specific feature, said predetermined bipolar pulse frequency is comprised between 0.5 and 10 Hz.

According to a specific feature, said predetermined bipolar pulse frequency is about 1 kHz.

According to a specific embodiment at least one activation step is followed by a recording step, in which a response of the brain tissue to said activation of said set of bipolar electrodes is recoded.

According to a specific embodiment, on the basis of a plurality of responses previously recorded, it comprises at least one computation step in which a Neural Network Excitability Index is calculated.

According to a specific embodiment, said at least one computation step comprises:
  dividing the LFP signal, included in recorded responses (RESP) during periodic pulse stimulation, into single response epochs s;
  applying, on each epoch s, a Fast Fourier Transform (FFT), yielding both the amplitude and phase of its frequency components, as complex-valued coefficients.
  at each stimulation frequency f, a Phase Clustering Index (PCI) is computed as the average of these complex coefficients, normalized by their magnitudes, over epochs:

$$PCI(f) = \left| \frac{<Z_f^s>_s}{\sqrt{<|Z_f^s|^2>_s}} \right|$$

obtaining said Neural Network Excitability Index (NNEI) by NNEI=1−PCI($f_s$)

According to a specific embodiment, the duration of an activation step last between 3 and 7 minutes.

According to a specific embodiment, about 300 activation step of said set of bipolar electrodes are performed, each followed by a recoding step, in which a response of the brain tissue to the preceding activation of said set of bipolar electrodes is recoded.

According to a specific embodiment, the method comprises:
- a set of a predetermined number of activation steps, each activation step being followed by a recording step in which a response of the brain tissue to said activation of said set of bipolar electrodes is recoded, where said predetermined bipolar pulse frequency is comprised between 0.5 and 10 Hz and where delivering e set of said predetermined number of response;
- a step of calculation of a Neural Network Excitability Index, for at least one sub-region of said brain tissue, as a function of said set of response; and
- when a value of said Neural Network Excitability Index is greater than 0.5 for said at least one sub-region of said brain tissue, a set of a predetermined number of activation steps, where said predetermined bipolar pulse frequency is about 1 kHz.

The invention also relates to a stimulation device. Such device comprises the necessary means for applying any combination of the previous embodiments.

According to the present technique, the device comprises an electronic circuit, a memory and a processor for repeatedly transmitting to a set of bipolar electrodes, an electric current at a predetermined intensity and at a predetermined frequency, delivering a predetermined electric current (between the anode and a cathode of each bipolar electrode of said set of electrodes), said predetermined electric current value inducing an activation of said GABAergic neurons and a minimized activation of other neuron types of said neural tissue.

According to an embodiment, the device also comprise means for recording the activity of said GABAergic neurons after at least one iteration of transmission of current to said set of bipolar electrodes.

According to a preferred implementation, the different steps of the methods according to the invention are implemented by one or more software programs or computer programs comprising software instructions to be executed by a data processor of a stimulation and recording device according to the invention and being designed to command the execution of the different steps of the methods.

Consequently, the invention is also relates to a program capable of being executed by a computer or a data processor, this program comprising instructions to command the execution of the steps of a method as mentioned here above.

This program can use any programming language whatsoever and can be in the form of a source code, object code or an intermediate code between source code and object code as in a partially compiled form, or in any other desirable form.

The invention is also aimed at providing an information carrier readable by a data processor and comprising instructions of a program as mentioned here above.

The information carrier can be any entity or device capable of storing the program. For example, the carrier can comprise a storage means such as a ROM, for example a CD ROM or a microelectronic circuit ROM or again a means of magnetic recording, for example a floppy disk or a hard disk drive.

Besides, the information carrier can be a transmissible carrier such as an electrical or optical signal, which can be conveyed via an electrical or optical cable, by radio or by other means. The program according to the invention can especially be downloaded from an Internet type network.

As an alternative, the information carrier can be an integrated circuit in which the program is incorporated, the circuit being adapted to executing or to being used in the execution of the method in question.

According to one embodiment, the invention is implemented by means of software and/or hardware components. In this respect, the term "module" in this document can correspond equally well to a software component as to a hardware component or to a set of hardware or software components.

A software component corresponds to one or more computer programs or several sub-programs of a program or more generally to any element of a program or a software package capable of implementing a function or a set of functions, according to what is described here above for the module concerned. Such a software component is executed by a data processor of a physical entity (terminal, server, gateway, router, etc) and is capable of accessing hardware resources of this physical entity (memory, recording media, communications buses, input/output electronic boards, user interfaces, etc).

In the same way, a hardware component corresponds to any element of a hardware assembly capable of implementing a function or a set of functions according to what is described here below for the module concerned. It may be a programmable hardware component or a component with an integrated processor for the execution of the software, for example an integrated circuit, a smartcard, a memory card, an electronic card for executing firmware, etc.

Each component of the method and apparatus described here above naturally implements its own software modules. The different embodiments mentioned here above can be combined with one another to implement the invention.

4. FIGURES

The proposed method and device are described in the following by way of examples in connection with the accompanying figures without limiting the scope of the protection as defined by the claim. The figures show:

5. DESCRIPTION

5.1. General Description

Figure 1:
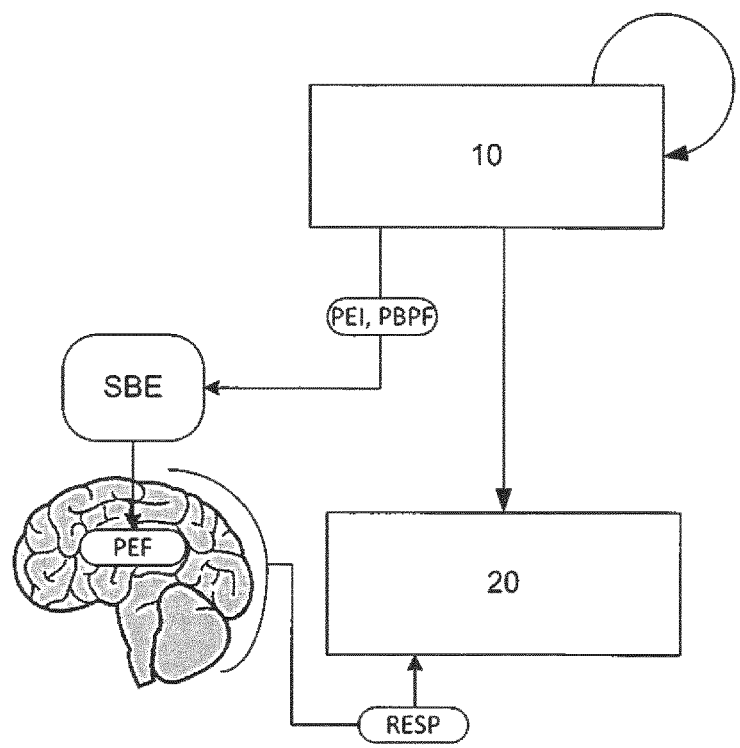
FIG. 1 is an illustration of the stimulation method according to one embodiment of the invention.

As already explained, the proposed method pertains to a local stimulation of brain tissue, performed with bipolar electrodes. In the proposed method, the critical factor is the electric field distribution and value, and not the stimulation intensity: the geometry of contacts, along with the distance between contacts are indeed determinant factors in the electric field distribution. The most important in the proposed method is to integrate the electrode design physical parameters and to provide, considering the integrated parameters, a predetermined electric field. The predetermined electric field depends on an electric potential value, which is measured during the stimulation.

From the biophysical point of view, what impacts the membrane potential of neurons is the electric field, and not the stimulation current directly. Therefore, the stimulation intensity on its own is meaningless in terms of neuronal activation.

In the disclosed embodiments, two types of stimulations are proposed. These two types of stimulations vary mainly by the frequency (of the biphasic pulse, also called the "biphasic pulse frequency") which is applied during the stimulation. In the first case, a low frequency is used (comprised between 0.5 and 10 Hz). In the second case, a (relatively) high frequency is used (about 1 Khz).

In both case, the optimal intensity range can be translated from kainate mice brain tissue to human brain tissue by calculating, for example, the equivalent in situ electric field induced by intracerebral electrodes in mice, and evaluating the required stimulation current to induce a comparable electric field in the human brain tissue.

This can be done by calculating the electrical potential induced by each of the stimulation contacts, and applying the superposition principle to calculate the equivalent electrical potential at each point in space. The electric field is then calculated as the opposite of the spatial gradient of the electrical potential. This translation of electric field values between mice and humans can be used since mice and human hippocampal neurons have very similar sizes and neurophysiological properties, both of which underlie the neurophysiological response to an applied electric field (e.g., membrane polarization).

There are two main types of neurons in the brain: excitatory and inhibitory. Excitatory neurons (pyramidal), mostly using glutamate as their neurotransmitter, can increase the activity of neurons they project their axons to. On the other hand, inhibitory neurons (typically using GABA as their neurotransmitter) will decrease the activity of neurons on which they project their axons. In a physiological context, there is a balance between excitation and inhibition. Dysregulation of GABAergic neurons leads to an imbalance between excitatory and inhibitory processes. Recording signals coming only from specific types of neurons may be difficult. Such recordings may be obtained using indirect processes, that is, for example, by measuring an overall signal and then "subtract" a known signal. This is one of the numerous applications of the proposed technique.

Thus, it's interesting to differentially activate either excitatory or inhibitory neurons, providing a window on the level of tissue excitability. In the proposed technique, the inventors exploit the fact that these GABAergic neurons have specific morphological (extended axonal branching) and electrophysiological properties (more depolarized resting membrane potential, higher input resistance) which make them more prone to discharge following low-intensity electrical stimulation.

The proposed technique is illustrated in relation with FIG. 1. In a general manner, the proposed techniques relates to a local stimulation method of a predetermined region of brain tissue, said brain tissue comprising at least GABAergic neuron type, said method comprises at least one activation step (10) of a set of bipolar electrodes (SBE), according to a predetermined electric intensity (PEI) and a predetermined biphasic pulse frequency (PBPF), inducing an electric field distribution (PEF), said electric field distribution (PEF), inducing an activation of said GABAergic type neurons and a minimal activation of other types of neurons.

According to a specific characteristic, the activation of said set of bipolar electrodes comprises delivering, to said bipolar electrodes, biphasic pulses, each biphasic pulse lasting about 200 microseconds.

According to a specific characteristic, at least one activation step (10) is followed by a recording step (20), in which a response (RESP) of the brain tissue to said activation of said set of bipolar electrodes is recoded.

In a general embodiment, each activation (10) of the plurality of activations is followed by one recording (20). The activation last a predetermined duration (between 3 and 7 minutes, e.g. 5 minutes), and the recording is made on a measurement of the signal which is obtained.

The proposed technique is illustrated in relation with FIG. 1. In a general manner, the proposed techniques relates to a local stimulation method of a predetermined region of brain tissue, said brain tissue comprising at least GABAergic neuron type, said method comprises at least one activation step (10) of a set of bipolar electrodes (SBE), according to a predetermined electric intensity (PEI) and a predetermined biphasic pulse frequency (PBPF), inducing an electric field (and/or field distribution (PEF)), said electric field (and or field distribution (PEF)), inducing an activation of said GABAergic type neurons and a minimal activation of other types of neurons. The terms "minimal activation" is a simple and concise way of telling "almost no stimulation of other types of neuron". It is known that considering the sizes of the neurons and the sizes of the electrodes, it is difficult to target specifics neurons in the brain tissue, since an electrode is far bigger than a neuron. Thus, it is also known, that while stimulating brain tissues, many types of neurons can be stimulated. An objective of the invention is to provide a method in which, considering what has been exposed before, "almost no stimulation of other types of neuron" will occur (thanks to the delivering a predetermined electric fields (PEF) and/or the predetermined electric field distribution). But of course, in the event the electrodes would be small enough, minimal activation would then be no activation at all.

In view of the goals of the stimulations, a predetermined number of activation (10) and recording (20) are implemented.

In another embodiment, a single recording (20) can be made after several simulations (10). This embodiment can be for example useful for monitoring the effects of several trains of stimulation without needing that the brain tissue which is tested remains connected to a recording device or system. This may also be useful for trying to understand the variation of the excitability of the brain tissue in time.

The various responses which are recorded after the stimulation (after the activations) may then be computed in order to calculate a Neural Network Excitability Index (NNEI). This index may be used for characterizing the brain tissue under stimulation. Such an index may then be used in various tasks.

According to a specific embodiment, the proposed method is used twice. More specifically, in this embodiment, the method comprises:
being followed by a recording step (20) in which a response (RESP) of the brain tissue to said activation (10) of said set of bipolar electrodes is recoded, where said predetermined bipolar pulse frequency (PBPF) is comprised between 0.5 and 10 Hz and where delivering e set of said predetermined number of response (RESP);
a step of calculation of a Neural Network Excitability Index (NNEI), for at least one sub-region of said brain tissue, as a function of said set of response (RESP); and
when a value of said Neural Network Excitability Index (NNEI) is greater than 0.5 for said at least one sub-region of said brain tissue, a set of a predetermined number of activation steps (10), where said predetermined bipolar pulse frequency (PBPF) is about 1 kHz.

5.2. Description of a First Embodiment

In this first embodiment, an example of the proposed method is disclosed at a relatively low biphasic pulse frequency (between 0.5 and 10 Hz).

In this embodiment of the method, the objective is to acquire (record) a given number of post-stimulation evoked responses (i.e to acquire and record a signal immediately following the stimulation). In this embodiment, trains of low-intensity electrical stimulation, lasting between 1 and 5 minutes, are used.

Gradually, the intensity is tuned to activate selectively GABAergic interneurons, on the order of 1.2 microamperes with intracerebral bipolar electrodes separated by 400 micrometers and a contact diameter of 120 micrometers in mice brain tissue. Since the tissue properties may change from one tissue to another, it may not be suitable to use directly the value of 1.2 microamperes with the given parameters. It may be different with other parameters, depending on the geometry of the bipolar electrodes and contacts.

It has to be noted that the method is not directed towards the implantation of the electrode in tissue, so it's not a surgical method. Instead, bipolar electrodes already implanted in brain tissue are used.

In human brain tissue, the intensity used is on the order of 0.3 milliamperes (in the specific case where stereoelectroencephalography (sEEG) intracranial electrodes are used, which feature contacts 2 mm high, 0.8 mm diameter, spaced by 1.5 mm).

In all cases (mice brain tissue, human brain tissue), the total biphasic pulse width is 200 microseconds (100 microseconds per phase). The biphasic pulse frequency is comprised between 0.5 and 10 Hz, and is adapted to the GABAergic neurons' response: above this frequency, they are not able to trigger systematic responses to each stimulation pulse. In a specific case, an intracranial EEG (LFP, local field potential) is recorded simultaneously in order to assist setting the optimal stimulation intensity.

Figure 2:
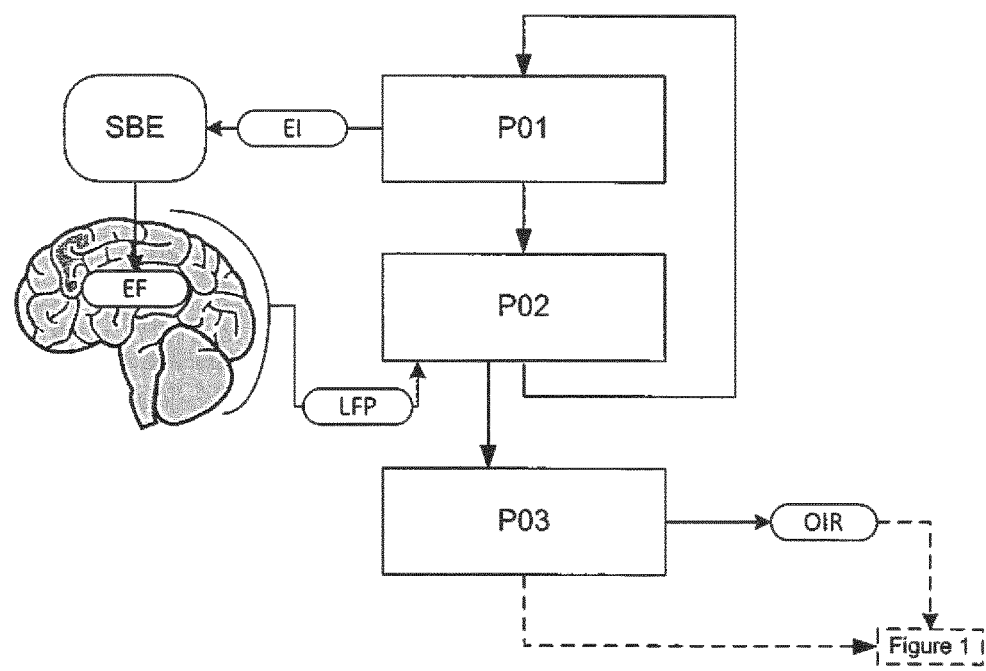
FIG. 2 illustrates a complementary stimulation tuning method according to a specific feature of the invention.

In this embodiment, described in relation with FIG. 2, for determining the correct intensity in view of the given parameters (i.e. the electrodes), and in view of the brain tissue which is studied, the following method is applied:
- intensity (EI) of the stimulation pulses is gradually increased (P01) while the LFP response to each pulse is recorded (P02): electric fields (EF) are then induced;
- on the basis of the LFP responses, the optimal intensity range (OIR) is evaluated (P03) as: in the optimal intensity range, each stimulation pulse systematically triggers a post-stimulation inhibitory response (negative deviation in the LFP signal); for lower intensity values, no post-stimulation inhibitory response is triggered, or not systematically; for higher intensity values, glutamatergic (excitatory) neurons are also recruited and the purely inhibitory response post-stimulation disappears; so, a negative deviation in the LFP signal implies that the applied intensity (IE) is in the range;
- once the optimal intensity range (OIR) has been evaluated, stimulation trains are delivered for a duration on the order of a couple of minutes, in order to acquire about predetermined number of response (RESP) of usable post-stimulation responses: this corresponds to the recording method, presented in relation with FIG. 1, for obtaining the post-stimulation responses, in which some intensity values of the optimal intensity range (OIR) are used as the predetermined electric intensity (PEI); the post-stimulation responses are also LFP responses (this is the same kind of responses).

The predetermined number of response (RESP) has to be sufficient for deriving a usable statistical index. The predetermined number may be comprised between 100 and 500; an average and usable number is about 300 (i.e. not too long to obtain).

These responses are recorded and, in themselves, they can be used for characterizing the brain tissue excitability. An example of such characterization is:
- post-stimulation evoked responses (about 300) are used to compute an index with a value between 0 and 1 (NNEI: "Neural Network Excitability Index"): this index quantifies the phase coherence of recorded responses; the way the index is obtained is described above;
- NNEI values close to 0 characterize a tissue that is weakly excitable; High NNEI values (e.g., 0.5 and above) characterize a highly excitable tissue.

5.2.1. Computation of the Neural Network Excitability Index (NNEI)

The NNEI is a normalized quantity (ranging from 0 to 1) that measures the phase similarity among signals. It is derived from the Fourier Transform (FT) which provides both the amplitude and the phase of oscillatory components present in the signals. In practice, the NNEI computation involves three steps.
- dividing the Local Field Potential (LFP) signal, included in recorded responses (RESP) during periodic pulse stimulation, into single response epoch s;
- applying, on each epoch s, a Fast Fourier Transform (FFT), yielding both the amplitude and phase of its frequency components, as complex-valued coefficients.
- at each stimulation frequency f, a Phase Clustering Index (PCI) is computed as the average of these complex coefficients, normalized by their magnitudes, over epochs:

$$PCI(f) = \left| \frac{<Z_f^s>_s}{\sqrt{<|Z_f^s|^2>_s}} \right|$$

- obtaining said Neural Network Excitability Index (NNEI) by NNEI=1−PCI ($f_s$)

Indeed, PCI(f) is close to zero for randomly distributed phases, and close to 1 for coherent phases. Finally, in order to derive from PCI($f_s$) an index that is congruent with the excitability levels, the NNEI is define by NNEI=1−PCI($f_s$), where $f_s$ denotes the stimulation frequency. The NNEI discloses low values, at low excitability levels, where LFP evoked responses (time locked to each pulse of the stimulation train) have similar time-courses, and high values, at high excitability levels, where LFPs have irregular time-courses, provided that the stimulation intensity is appropriately tuned.

5.2.2. Statistical Test for Optimal Stimulation Intensity

The optimal intensity value corresponds to the intensity for which the cross-correlation among stimulation evoked LFP responses becomes significant, and thus the null-hypothesis, ($H_0$: $\rho_{xy}^i$=0), can be rejected. The proposed test starts with the computation of the value $r_{xy}^i$ of the linear correlation coefficient for any pair i of evoked responses X and Y. A log-transform of $r_{xy}^i$ is introduced:

$$\gamma^i = \frac{1}{2} \ln\left[\frac{(1+r_{xy}^i)}{(1-r_{xy}^i)}\right]$$

It can be shown that the obtained random variable $\gamma^i$ is normally distributed with mean $$m_{\gamma^i} = \frac{1}{2}\ln\left[\frac{(1+p^i_{xy'})}{(1-p^i_{xy'})}\right]$$

and variance $$\sigma^2 = \frac{1}{(m-3)}$$

under the null hypothesis ($H_0$: $\rho_{xy'}^i=0$), where m is the size of evoked LFP responses (# samples).

The sum $\Gamma$ of $\gamma^i$ values over the $$N = \frac{n(n-1)}{2}$$

pairs of evoked responses (for simplicity considered as independent) recorded from a stimulation train of n pulses is also Gaussian:

$$\Gamma \sim \mathcal{N}\left(\sum_{i=1}^{N} m_{\gamma^i}, \sum_{i=1}^{N} \sigma^2_{\gamma^i}\right)$$

Thus, the acceptance region at the (1−p) level of confidence for the hypothesis of absence of correlation among evoked responses is given by:

$$-z_{p/2} \leq w = \frac{\sqrt{m-3}}{2N}\sum_{i=1}^{N}\ln\left[\frac{(1+r^i_{xy'})}{(1-r^i_{xy'})}\right] \leq z_{p/2}$$

where z is the normalized variable. It follows that values outside the interval [−2.576, +2.576] constitute evidence for the existence of a correlation between evoked responses at 99% level of confidence (p-value=0.01, $z_{0.005}$=−2.576).

The evolution of the NNEI computed from simulated LFPs, for three excitability states (low, med and high) and for three stimulation intensity values (optimal, optimal divided by 3 and optimal times 3). The optimal I-value (1.5 a.u) was that corresponding to w=2.6 (i.e. just above statistical threshold 2.576). As depicted, for this precise intensity, the NNEI can effectively discriminate the three excitability states. In contrast, when the intensity is too low (w<<2.576) or two high (w>>2.576), NNEI values are not indicative of the excitability level in the model.

5.3. Description of a Second Embodiment

In this embodiment of the method, the objective is to acquire (to record) a given number of post-stimulation responses (i.e acquire a signal after the stimulation, and then to record it). In this embodiment, trains of higher intensity than NNEI, consisting in a repetition of trains lasting several minutes each (e.g. 5 minutes). The stimulation trains are separated by several minutes. The frequency is on the order of 1000 Hz, optimized to reduce the number of markers (e.g., in mice, hippocampal paroxysmal discharges, HPD; which are more frequent/longer in duration when excitability increases) present in the signal.

For significantly lower stimulation frequency (e.g., 100 Hz), no significant decrease of HPD is observed. Pulse width is, as in the previous embodiment, 200 microseconds (total width of the biphasic pulse, 100 microseconds per phase).

In this embodiment, a type of markers is selected in order to quantify the efficiency of the stimulation. The marker can be, for example, hippocampal paroxysmal discharges (HPD) in a (kainate) mice.

An EEG (for example an intracranial EEG (LFP)) is recorded simultaneously in order to assess stimulation efficiency, as quantified by the number of markers present in the signal.

The intensity used can be 5 microamperes or higher (significant HPD decreases observed for intensity values of 10-20 microamperes in kainate mice, with intracerebral bipolar electrodes (twisted wires) separated by 400 micrometers and a contact diameter of 120 micrometers in mice.

In this embodiment, to obtain the correct intensity in view of the given parameters (i.e. the electrodes) and in view of the brain tissue which is studied, the following method is applied:
- the intensity of the stimulation is gradually increased every couple of blocks (e.g., every 2 blocks), while the EEG is recorded between two stimulation pulses;
- the number of HPD is quantified (number of HPD per unit of time) for each EEG recording block (between stimulation blocks);

The following stimulation results are obtained:
- in the optimal intensity range, the HPD rate decreases with increasing stimulation intensity; outside of the optimal intensity range, the number of HPD rate is not modified by the stimulation, or may even increase.
- in the correct stimulation polarity, the number of HPD rate decreases, while in the other stimulation polarity the occurrence rate of markers can increase (e.g., increase in the number of spikes or HPD per unit of time). Therefore, this could be also used as a way to probe the hyperexcitability of regions, in which the number of markers is increased.

5.4. Description of Corresponding Device

Figure 3:
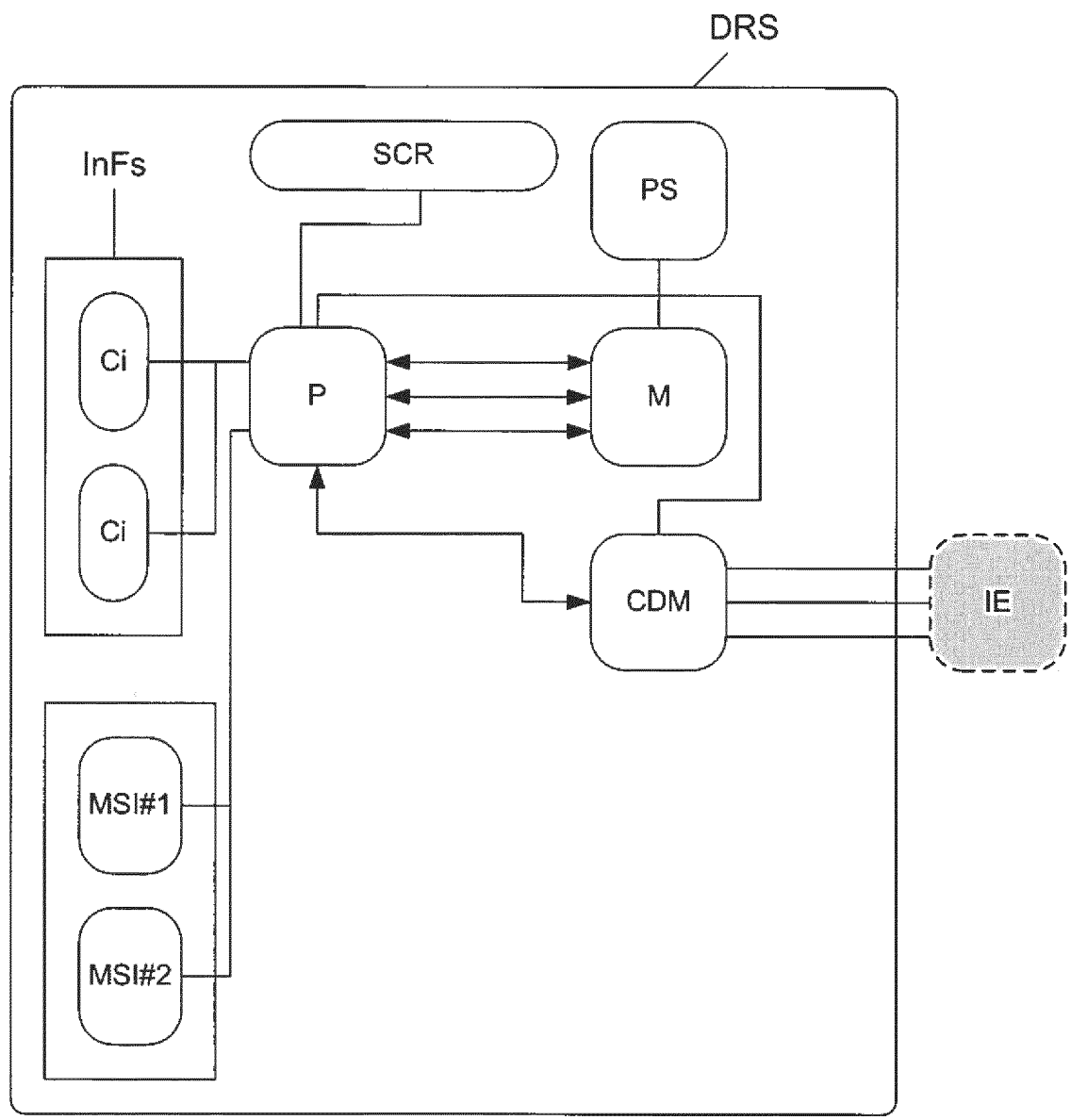
FIG. 3 illustrates a specific device implementing the method of the invention.

In another embodiment, the proposed technique also relates to a device. The device may be used, in situ, for recording stimulation effects occurring when aforementioned methods are used. More generally, the device comprises the necessary means for implementing the aforementioned methods. A typical example is the use of the previous method on a patient, said patient having already been implanted with intracranial electrodes. There may be an interest in recording the effects of the stimulations in a conventional environment (e.g. outside a hospital). The proposed device may then be connected to the electrodes and may be used for transferring stimulation impulsions to the electrodes, as a function of a predetermined scheme: for example a scheme with use low frequencies of biphasic pulse (first embodiment of the method) or a scheme which use high frequencies of biphasic pulse (second embodiment of the method) or a scheme which implements one or more iterations of both methods, in view of the results which are sought. Thus, the device may be wearable. The device is described in relation with FIG. 3.

Concretely, a device (DRS) of this type comprises a processor (P), coupled to a memory (M), said memory comprising at least one set of instructions for driving the electrical stimulation, according to the proposed methods. The processor comprises a connection to at least an electric current delivering module (CDM), said electric current delivering module (CDM) being connectable to intracranial electrodes (IE) which have already been installed on the patient. The processor (P), the circuitries, the electric current delivering module (CDM), and the other components of the device, are connected to a power source (PS). The power source (PS) may take the form of an internal battery or of an external battery. The battery is for example an ion polymer battery, or the like, which is able to deliver an electric current suitable for the functioning of the components of the device.

The device may also comprise a plurality of interfaces (InFs) for implementing additional functionalities. Thus, the device may comprise a first communication interface (CI), which is connected to at least one recording device or system. This first communication interface (CI) can have two functions: the first function is to transmit, to the recording device, data related to the parameters of the stimulations. This can be useful when the recording device needs to calibrate itself as a function of these parameters. The second function is to receive, from a recording device, the recorded data. For example, when the recording device is an EEG helmet, the recording device may need to transmit the recorded data to another device. Hence, the stimulation device may play the role of a recording unit. This is useful for example in a standalone implementation. The patient does not need, then, to be attached to a specific location and remains autonomous. In such a case, it may then be considered that the interface also comprises a power delivering source for delivering the electric current necessitated by the recording device.

The device may also comprise one or two mass storage interfaces (MSI #1, MSI #2). These interfaces may be use for several purposes. The first one (MSI #1) is the recording of the stimulation in itself, either by the use of an external recording device or by the use of an integrated recording device. The second one (MSI #2) allows enabling the device to receive new stimulation parameters, for example by the update of a microcode program or by the transmission of a file comprising the new parameters.

The device may also comprise a screen (SCR). This screen may be suitable for verifying the state of the power source (e.g. the battery) and the various parameters of the stimulation. When linked to an external recording device or system (like an EEG helmet), the device also comprises means for transmitting recording instructions to the recording device. These means are for example a serial interface or an USB interface. These instructions are for example transmitted at the end of a stimulation train (at the end of a period of stimulation), for recording the signal obtained after one or several trains of stimulations. The device also comprises means for analyzing the signal received by the recording device. In this context, the device may also comprise means for processing the received signal, for example to calculate a Neural Network Excitability Index (NNEI) or the number of markers present in the signal. These means may take the form of a specialized processor. The screen (SCR) may then be used for displaying the indexes or the markers.

The means are driven by (or included in) the processor, which comprises a hardware or software module for implementing the previous methods.

Additionally, the device may also comprise communication means, linked to communication interfaces (CI). These means may take the form of a WiFi or Bluetooth (low energy) module. The purpose of these means is to be able to communicate with another device, which may be for example a smartphone or a tablet or a server. The analysis of the results or the calculations of the indexes and/or the markers may then be made by the other device. This has several advantages: the stimulation device is then cheaper to manufacture and it can be used in a wide range of situation. Another advantage is to be able to use the storage space of the other device for recording the various data produced by the stimulation device. Another advantage is to be able to manage the device remotely.

Of course, the device comprises all the necessary means for implementing the proposed method. To this end, it is proposed a local stimulation device, for stimulating of a predetermined region of brain tissue, said brain tissue comprising at least GABAergic neuron type. The device comprises activation means (10) of a set of bipolar electrodes (SBE), according to a predetermined electric intensity and a predetermined biphasic pulse frequency (PBPF), delivering predetermined electric field, said predetermined electric field (PEF), inducing a predominant activation of said GABAergic type neurons.

In a specific embodiment, activation means of said set of bipolar electrodes deliver, to said bipolar electrodes, biphasic pulses, each biphasic pulse lasting about 200 microseconds.

In a specific embodiment, said predetermined bipolar pulse frequency (PBPF) is comprised between 0.5 and 10 Hz.

In a specific embodiment, said predetermined bipolar pulse frequency (PBPF) is about 1 kHz.

In a specific embodiment, the device comprises recording means (20), by which a response (RESP) of the brain tissue to said activation (10) of said set of bipolar electrodes by the activation means is recorded.

In a specific embodiment, the device comprises computation means for calculating a Neural Network Excitability Index (NNEI) on the basis of a plurality of responses (RESP) previously recorded by said recording means.

In a specific embodiment, the computation means comprises means for:
- dividing the LFP signal, included in recorded responses (RESP) during periodic pulse stimulation, into single response epochs s;
- applying, on each epoch s, a Fast Fourier Transform (FFT), yielding both the amplitude and phase of its frequency components, as complex-valued coefficients.
- at each stimulation frequency f, a Phase Clustering Index (PCI) is computed as the average of these complex coefficients, normalized by their magnitudes, over epochs:

$$PCI(f) = \left| \frac{<Z_f^s>_s}{\sqrt{<|Z_f^s|^2>_s}} \right|$$

obtaining said Neural Network Excitability Index (NNEI) by $NNEI = 1 - PCI(f_s)$ In a specific embodiment, the activation means are configured so that the duration of an activation of the activation means last between 3 and 7 minutes.

In a specific embodiment, the activation means are configured for performing about 300 activation of said set of bipolar electrodes, each followed by the activation of the recoding means, in which a response of the brain tissue to the preceding activation of said set of bipolar electrodes is recoded.

In a specific embodiment, said device is configured for:
performing a set of a predetermined number of activation (10) of said set of bipolar electrodes (SBE), each activation (10) being followed by using the recording means for recording (20) a response (RESP) of the brain tissue to said activation (10) of said set of bipolar electrodes, where said predetermined bipolar pulse frequency (PBPF) is comprised between 0.5 and 10 Hz and where delivering e set of said predetermined number of response (RESP);
calculating a Neural Network Excitability Index (NNEI), for at least one sub-region of said brain tissue, as a function of said set of response (RESP) recoded by said recording means; and
when a value of said Neural Network Excitability Index (NNEI) is greater than 0.5 for said at least one sub-region of said brain tissue, performing a set of a predetermined number of activation steps (10), where said predetermined bipolar pulse frequency (PBPF) is about 1 kHz.

The invention claimed is:

1. A local stimulation method of a predetermined region of brain tissue to characterize the brain tissue under stimulation, said brain tissue comprising at least GABAergic neuron type, said method comprising a main set of steps comprising:
performing a predetermined number of first activation steps using a set of bipolar electrodes by delivering a first predetermined electric field with a first predetermined electric intensity and a first predetermined biphasic pulse frequency comprised between 0.5 and 10 Hz, wherein said first predetermined electric field induces an activation of said GABAergic type neurons;
after each of the first activation steps, performing a recording step, in which a response of the brain tissue to said activation is recorded, wherein the set of predetermined first activation steps delivers said predetermined number of responses; and
performing a step of characterization on the basis of a plurality of said recorded predetermined number of responses to evaluate the excitability of GABAergic type neurons of said brain tissue, said step of characterization comprising:
a step of calculating a Neural Network Excitability Index (NNEI), for at least one sub-region of said brain tissue, as a function of said predetermined number of responses; and
when a value of said NNEI is greater than 0.5 for said at least one sub-region of said brain tissue, a set of predetermined number of second activation steps is performed with a second predetermined biphasic pulse frequency of about 1 kHz.

2. The local stimulation method according to claim 1, wherein the activation of said set of bipolar electrodes comprises delivering, to said bipolar electrodes, biphasic pulses, each biphasic pulse lasting about 200 microseconds.

3. The local stimulation method according to claim 1, wherein, the calculation of said NNEI by NNEI=1−PCI($f_s$) comprises:
dividing a local field potential signal, included in the recorded responses during periodic pulse stimulation, into single response epochs (s);
applying, on each s, a Fast Fourier Transform, yielding both amplitude and phase of its frequency components, as complex-valued coefficients (Z); and
at each of the first predetermined biphasic pulse frequency (f), a Phase Clustering Index (PCI) is computed as an average of these complex coefficients, normalized by their magnitudes, over s:

$$PCI(f) = \left| \frac{<Z_f^s>_s}{\sqrt{<|Z_f^s|^2>_s}} \right|.$$

4. The local stimulation method according to claim 1, wherein a duration of the first and/or second activation step lasts between 3 and 7 minutes.

5. The local stimulation method according to claim 1, wherein the number of the predetermined number of responses is about 300.

6. A local stimulation device, for stimulating a predetermined region of brain tissue, said brain tissue comprising at least GABAergic neuron type, said device comprising:
a processor; and
a non-transitory computer-readable medium comprising instructions stored thereon, which when executed by the processor configure the local stimulation device to perform acts comprising:
performing a predetermined number of first activation steps using a set of bipolar electrodes by delivering a first predetermined electric field with, according to a first predetermined electric intensity and a first predetermined biphasic pulse frequency comprised between 0.5 and 10 Hz wherein, said first predetermined electric field induces an activation of said GABAergic type neurons;
after each of the first activation steps, performing a recording step, in which a response of the brain tissue to said activation is recorded, wherein the set of predetermined first activation steps delivers said predetermined number of responses; and
performing a step of characterization on the basis of a plurality of said recorded predetermined number of responses to evaluate the excitability of GABAergic type neurons of said brain tissue, said step of characterization comprising:
a step of calculating a Neural Network Excitability Index (NNEI), for at least one sub-region of said brain tissue, as a function of said predetermined number of responses; and
when a value of said NNEI is greater than 0.5 for said at least one sub-region of said brain tissue, a set of predetermined number of second activation steps is performed with a second predetermined biphasic pulse frequency of about 1 kHz.

7. The local stimulation device according to claim 6, which further comprises:
a power source;
an external communication interface;
an electric current delivering module having a connection to the processor, said electric current delivering module being connectable to the set of bipolar electrodes, which are intracranial electrodes, the processor and the electric current delivering module being connected to the power source, said instructions configuring the local stimulation device for implementing a local stimulation of said predetermined region of brain tissue, according to stimulation parameters which are provided to said device via the external communication interface.

8. A non-transitory computer-readable medium comprising instructions of program code for implementing a local stimulation method when run on a computing device, wherein the method comprises:

local stimulation of a predetermined region of brain tissue, said brain tissue comprising at least GABAergic neuron type, said simulation comprising:

performing a predetermined number of first activation steps using a set of bipolar electrodes by delivering a first predetermined electric field with, according to a first predetermined electric intensity and a first predetermined biphasic pulse frequency comprised between 0.5 and 10 Hz wherein, said first predetermined electric field induces an activation of said GABAergic type neurons;

after each of the first activation steps, performing a recording step, in which a response of the brain tissue to said activation is recorded, wherein the set of predetermined first activation steps delivers said predetermined number of responses; and performing a step of characterization on the basis of a plurality of said recorded predetermined number of responses to evaluate the excitability of GABAergic type neurons of said brain tissue, said step of characterization comprising:

a step of calculating a Neural Network Excitability Index (NNEI), for at least one sub-region of said brain tissue, as a function of said predetermined number of responses; and when a value of said NNEI is greater than 0.5 for said at least one sub-region of said brain tissue, a set of predetermined number of second activation steps is performed with a second predetermined biphasic pulse frequency of about 1 kHz.

9. The local stimulation method of claim 1, wherein said main set of steps is preceded by a preliminary set of steps aiming at determining said first predetermined electric intensity, said preliminary set of steps including:

activating, a set of preliminary stimulating pulses, wherein an intensity of the preliminary stimulation pulses being gradually increased;

recording a Local Field Potential (LFP) response to each of the preliminary stimulating pulses;

evaluating an optimal intensity range based on an analysis of said LFP responses, the preliminary intensity being in the optimal range if the LFP signal presents a negative deviation; and selecting at least one of said first predetermined electric intensity within said optimal intensity range.

10. The local stimulation method according to claim 9, wherein the number of the predetermined number of responses in the main set of steps is between 100 and 500.

11. The local simulation method according to claim 10, wherein the number of the predetermined number of responses in the main set of steps is about 300.

* * * * *